(12) United States Patent
Dalal et al.

(10) Patent No.: US 7,731,658 B2
(45) Date of Patent: Jun. 8, 2010

(54) GLYCEMIC CONTROL MONITORING USING IMPLANTABLE MEDICAL DEVICE

(75) Inventors: Yousufali H. Dalal, Irvine, CA (US); Haresh G. Sachanandani, Shoreview, MN (US); Gerrard M. Carlson, Champlin, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 11/839,638

(22) Filed: Aug. 16, 2007

(65) Prior Publication Data

US 2009/0048503 A1 Feb. 19, 2009

(51) Int. Cl.
*A61B 5/02* (2006.01)
*A61B 5/00* (2006.01)
*A61N 1/00* (2006.01)

(52) U.S. Cl. .................... 600/365; 600/528; 607/22

(58) Field of Classification Search .................. 600/365, 600/513, 528; 607/3, 6, 19, 22, 32, 60, 62
See application file for complete search history.

(56) References Cited

U.S. PATENT DOCUMENTS

| | | | |
|---|---|---|---|
| 5,674,256 A | 10/1997 | Carlson | |
| 5,741,211 A | 4/1998 | Renirie et al. | |
| 6,044,298 A | 3/2000 | Salo et al. | |
| 6,058,329 A | 5/2000 | Salo et al. | |
| 6,298,269 B1 | 10/2001 | Sweeney | |
| 6,539,262 B2 | 3/2003 | Sweeney | |
| 6,643,548 B1 | 11/2003 | Mai et al. | |
| 6,650,940 B1 | 11/2003 | Zhu et al. | |
| 6,757,563 B2 | 6/2004 | Sweeney | |
| 7,029,443 B2 | 4/2006 | Kroll | |
| 7,052,466 B2 | 5/2006 | Scheiner et al. | |
| 7,113,825 B2 | 9/2006 | Pastore et al. | |
| 7,115,096 B2 | 10/2006 | Siejko et al. | |
| 7,123,962 B2 | 10/2006 | Siejko et al. | |
| 7,209,786 B2 | 4/2007 | Brockway et al. | |
| 7,228,175 B2 | 6/2007 | Jain et al. | |
| 7,248,923 B2 | 7/2007 | Maile et al. | |
| 7,260,429 B2 | 8/2007 | Siejko et al. | |

(Continued)

OTHER PUBLICATIONS

Schwingshandl, et al., "Echocardiographic Load-Independent Indices of Contractility in Children and Adolescents with Type I Diabetes: Effect of Metabolic Control and Insulin on Left Ventricular Performance", *Pediatric Cardiology*, vol. 16, No. 1, pp. 1-5 (Abstract only) Jan. 1995, 1 page.

*Primary Examiner*—Charles A Marmor, II
*Assistant Examiner*—Christian Y Jang
(74) *Attorney, Agent, or Firm*—Pauly, DeVries, Smith & Deffner, L.L.C.

(57) ABSTRACT

An apparatus for monitoring a patient's blood glucose level. The apparatus includes an implantable medical device having a controller and an implantable heart sounds sensor configured to transmit signals to the controller of the implantable medical device. The controller is configured to determine if a patient is hypoglycemic or hyperglycemic based on the signals from the heart sounds sensor. A method is also disclosed that includes sensing the patient's heart sounds, determining the amplitude of the S2 heart sound, determining the length of the interval from the S1 heart sound to the $S2_{max}$ heart sound, determining the length of the interval from the S1 heart sound to the $S2_{end}$ heart sound, and determining the patient's blood glucose status based on the patient's heart sounds.

20 Claims, 8 Drawing Sheets

U.S. PATENT DOCUMENTS

| | | | |
|---|---|---|---|
| 2003/0095263 A1* | 5/2003 | Varshneya et al. | 356/477 |
| 2003/0208240 A1* | 11/2003 | Pastore et al. | 607/17 |
| 2004/0077962 A1* | 4/2004 | Kroll | 600/513 |
| 2004/0127792 A1 | 7/2004 | Siejko et al. | |
| 2004/0230129 A1* | 11/2004 | Haefner | 600/510 |
| 2005/0049492 A1 | 3/2005 | Sweeney et al. | |
| 2005/0137490 A1 | 6/2005 | Scheiner et al. | |
| 2005/0148896 A1 | 7/2005 | Siejko et al. | |
| 2005/0283195 A1 | 12/2005 | Pastore et al. | |
| 2006/0025699 A1* | 2/2006 | Maile et al. | 600/528 |
| 2006/0161070 A1 | 7/2006 | Siejko et al. | |
| 2006/0167518 A1 | 7/2006 | Gill et al. | |
| 2006/0167519 A1* | 7/2006 | Gill et al. | 607/25 |
| 2006/0253159 A1 | 11/2006 | Siejko et al. | |
| 2006/0270939 A1 | 11/2006 | Wariar et al. | |
| 2006/0276849 A1 | 12/2006 | Carlson et al. | |
| 2006/0282000 A1 | 12/2006 | Zhang et al. | |
| 2007/0027400 A1 | 2/2007 | Carlson et al. | |
| 2007/0043299 A1 | 2/2007 | Wariar et al. | |
| 2007/0078491 A1 | 4/2007 | Siejko et al. | |
| 2007/0123943 A1 | 5/2007 | Patangay et al. | |
| 2007/0162080 A1 | 7/2007 | Brockway et al. | |
| 2007/0208390 A1 | 9/2007 | Von Arx et al. | |

* cited by examiner

| STATE \ MEASURE | S2 OR S3 AMPLITUDE (ST-SEGMENT) | S1-S2$_{MAX}$ OR V(SENSE)-S2$_{MAX}$ (QT$_{MAX}$) | S1-S2$_{END}$ OR V(SENSE)-S2$_{END}$ (QT$_{END}$) |
|---|---|---|---|
| HYPOGLYCEMIA | SIGNIFICANT DEVIATION | LENGTHENS | LENGTHENS |
| HYPERGLYCEMIA | SIGNIFICANT DEVIATION | LITTLE OR NO CHANGE | LITTLE OR NO CHANGE |
| CARDIAC ISCHEMIA | SIGNIFICANT DEVIATION | SHORTENS | LITTLE OR NO CHANGE |

GLYCEMIC CONTROL MONITORING USING IMPLANTABLE MEDICAL DEVICE

FIELD OF THE INVENTION

The invention relates to glycemic control in diabetic patients, and more particularly, to the use of an implantable medical device for monitoring glycemic control.

BACKGROUND OF THE INVENTION

Diabetes is a relatively common affliction in which a person's body does not produce or properly use the hormone called insulin that is needed to convert sugar, starches and other food into energy. By some estimates, about seven percent of the population of the United States has diabetes. The symptoms of diabetes are often not recognized, and it is estimated that about one-third of people with the disease do not realize they have it.

Compared to the general population, diabetes is estimated to be even more common within the population of patients who have an implanted cardiac rhythm management device. In one estimate, approximately 11-13% of patients with implantable pacemakers have diabetes, approximately 30-38% of patients having implantable cardioverter defibrillators have diabetes, and approximately 39-45% of patients having cardiac resynchronization therapy (CRT) devices have diabetes.

It is important that diabetic patients monitor their blood sugars (i.e., glucose). Because diabetes prevents the patient's body from naturally regulating blood sugars, the diabetic patient must administer insulin in response to blood sugar levels. Failure to closely monitor blood sugars can result in dangerous conditions of hypoglycemia (blood sugar level too low) or hyperglycemia (blood sugar level too high).

Hypoglycemia is where the patient's blood glucose level is too low. Hypoglycemia can result in unpleasant symptoms, such as dizziness or shakiness, and in severe cases, can result in dangerous symptoms such as loss of consciousness, brain damage, or death. These symptoms generally result from insufficient glucose in the blood stream to the brain, thereby diminishing the brain's function. Hypoglycemia can result from excessive insulin injection. Insulin affects the ability of the body's cells to use and consume glucose, such that insulin injections can cause the cells to use too much glucose from the blood stream too quickly, resulting in a deficiency.

Hyperglycemia is where the patient's blood glucose level is too high. Sustained high blood glucose levels can cause damage to the blood vessels and to the organs. Shorter term symptoms of hyperglycemia can result in frequent thirst, hunger, and urination, as well as fatigue, weight loss, and other symptoms. Acute hyperglycemia can result in ketoacidosis, which is where the patient's liver breaks down fats and proteins in response to a perceived need for more glucose in the bloodstream. However, the problem in a diabetic patient is generally that the patient lacks the insulin needed to use glucose, not that the blood glucose level is too low. However, the body's response is to resort to drastic measures to increase the blood glucose level, and in doing so, the patient's blood glucose level becomes elevated above a desired range.

Managing diabetes is largely about managing blood glucose levels. However, continuous testing of blood glucose levels is difficult. Most patients use a finger prick type blood glucose meter that draws a small sample of blood and analyzes it for glucose content. However, this requires patient involvement and is inconvenient and unpleasant for the patient. In some cases, the patient's compliance with the testing protocol is poor. Implantable blood glucose sensors are in development that could be used to continuously monitor blood glucose levels, however, despite extensive research and development efforts, the long-term functionality of these sensors is poor.

Improved techniques are needed for monitoring blood glucose levels of a patient.

SUMMARY OF THE INVENTION

In one aspect, an apparatus for monitoring a patient's blood glucose level is disclosed. The apparatus includes an implantable medical device having a controller and an implantable heart sounds sensor configured to transmit signals to the controller of the implantable medical device. The controller is configured to determine if a patient is hypoglycemic or hyperglycemic based on the signals from the heart sounds sensor.

In another aspect, a method for monitoring a patient's blood glucose level is disclosed. The method includes sensing the patient's heart sounds, determining the amplitude of at least one heart sound, determining the length of a time interval that ends at the $S2_{max}$ heart sound, and determining the length of a time interval that ends at the $S2_{end}$ heart sound. The method further includes determining the patient's blood glucose status based on the patient's heart sounds.

The invention may be more completely understood by considering the detailed description of various embodiments of the invention that follows in connection with the accompanying drawings.

While the invention may be modified in many ways, specifics have been shown by way of example in the drawings and will be described in detail. It should be understood, however, that the intention is not to limit the invention to the particular embodiments described. On the contrary, the intention is to cover all modifications, equivalents, and alternatives following within the scope and spirit of the invention as defined by the claims.

DETAILED DESCRIPTION OF THE INVENTION

As discussed above, a significant number of patients with diabetes also have an implantable medical device for treating a medical condition. Implantable medical devices (IMDs) are devices designed to be implanted into a patient. Some examples of these devices include cardiac rhythm management (CRM) devices such as implantable pacemakers, implantable cardioverter defibrillators (ICDs), cardiac resynchronization therapy (CRT) devices, and devices that include a combination of such capabilities. The devices are typically used to treat patients using electrical therapy and to aid a physician or caregiver in patient diagnosis through internal monitoring of a patient's condition. The devices may include electrodes in communication with sense amplifiers to monitor cardiac electrical activity within a patient, and often include sensors to monitor other internal patient parameters. Other examples of implantable medical devices include implantable diagnostic devices, implantable insulin pumps, devices implanted to administer drugs to a patient, or implantable devices with neural stimulation capability.

Cardiac Activity, Heart Sounds, and Blood Glucose Levels

Figure 1:
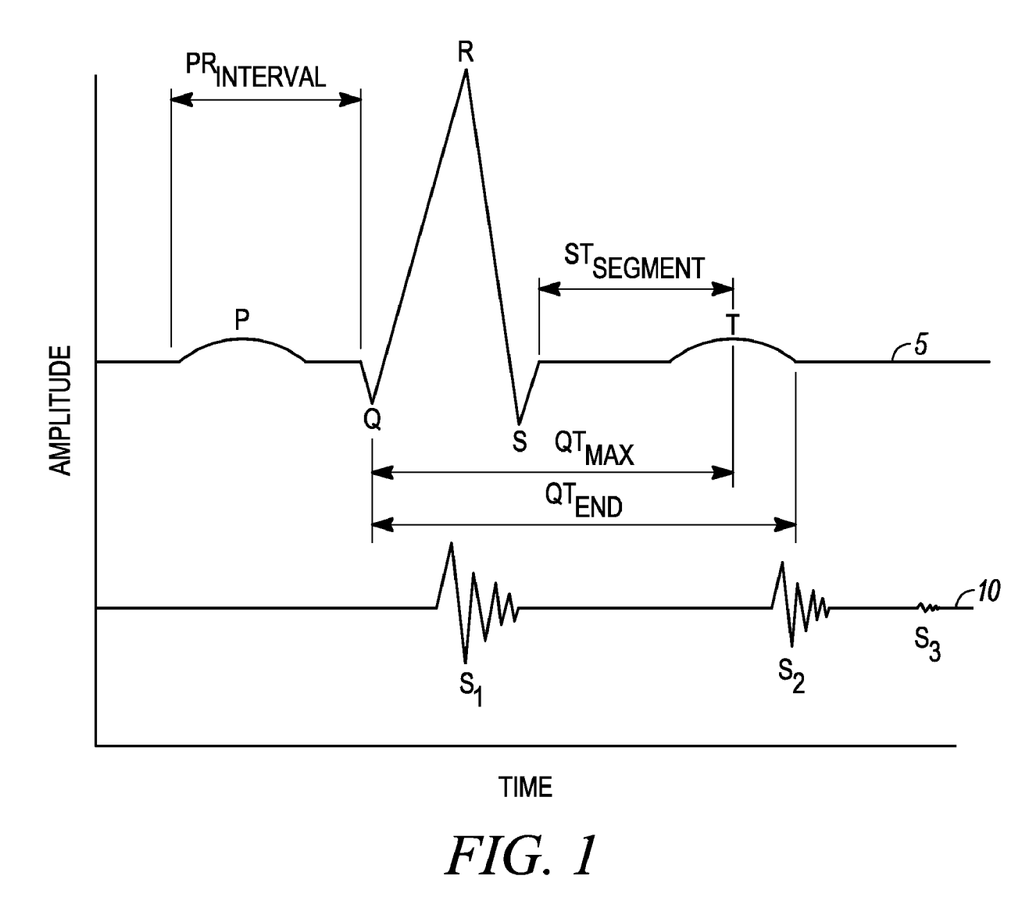
FIG. 1 is a demonstrative plot of typical characteristics of an electrocardiogram and heart sounds.

Cardiac activity can be characterized by a recording of the electrical signals from the heart. These signals can be called an electrocardiogram or an intracardiac electrogram, or just cardiac electrical signals. A typical cardiac electrical signal 5 is shown in FIG. 1. The P wave represents atrial depolarization, and the short flat segment after the P wave represents the passage of the electrical current through the AV node. The P-R interval starts at the beginning of the P wave and ends at the beginning of the QRS complex. The P-R interval represents the total time of atrial activity prior to ventricular activation. The QRS complex corresponds to the ventricular depolarization, and because of the relatively greater muscle mass of the ventricles, the QRS complex has a greater amplitude than the P wave. The S-T segment is the time between ventricular depolarization and repolarization, where this time begins at the end of the QRS complex and ends at the beginning of the T wave. The T-wave represents repolarization of the ventricles.

The QT interval is the time from the beginning of the QRS complex to the end of the T wave. The QT interval represents the total ventricular activity, from the time of the beginning of depolarization to the end of the repolarization. The QT interval varies as a function of the heart rate, where the faster the heart rate, typically the shorter the QT interval time. This is because at faster heart rates the repolarization is also faster. To account for the variability of the QT interval with heart rate, the QT interval is often corrected or normalized for heart rate so that various QT measurements can be compared. One way to calculate a corrected QT interval, commonly referred to as QTc, is to divide the actual measured QT interval by the square root of the heart rate. Symbolically, this is often represented as: $QT_c = QT/\sqrt{RR}$. Other formulas for determining a corrected QT interval are also used. The QT interval, when measured as described above to the end of the T wave, is sometimes called $QT_{end}$. In some cases, it is desired to also measure a separate parameter that is the time from the beginning of the QRS complex to the maximum repolarization or apex of the T wave. This parameter may be referred to as $QT_{max}$ or $QT_{apex}$. These parameters $QT_c$ and $QT_{max}$ are generally also corrected for heart rate by dividing by the square root of heart rate.

Cardiac activity further produces heart sounds that can be monitored. Heart sounds are associated with mechanical vibrations from activity of a patient's heart and the flow of blood through the heart. Heart sounds recur with each cardiac cycle and are separated and classified according to the activity associated with the vibration. Typical heart sounds 10 are shown on FIG. 1, where the position of the heart sounds indicates their typical occurrence with respect to the electrocardiogram. The first heart sound (S1) is the vibrational sound made by the heart during tensing of the mitral (AV) valve. The sound derives not from the closing of the valve itself, but rather from the vibrations induced into the walls of the ventricles and arteries when the blood is forced to stop suddenly because of the closure of the valve. The first heart sound indicates the onset of ventricular systole. When heard through a stethoscope, the first heart sound is low-pitched, soft, and relatively long, having a sound like "lub." The second heart sound (S2) derives from the closing of the semilunar (aortic and pulmonary) valves and marks the beginning of diastole. When heard through a stethoscope, the second heart sound is higher pitch, shorter, and sharper than the first heart sound, and has a sound like "dub."

There are other heart sounds that are occasionally or rarely heard. A third heart sound (S3) derives from the rush of blood into the left ventricle at the beginning of diastole. Although normal in children and young adults, the presence of an S3 heart sound tends to indicate congestive heart failure in older patients. A fourth heart sound (S4) is related to filling pressures of the left ventricle during diastole, and occurs just after atrial contraction. S4 is rarely heard, and is usually related to a failing left ventricle.

Heart sounds can be perceived or monitored in a number of different ways. In one embodiment, heart sounds can be measured with an implantable device. Techniques for measuring heart sounds with an implantable medical device are disclosed in Published United States Patent Application 2006/0282000, the contents of which are incorporated by reference in their entirety. For example, heart sounds can be measured with an accelerometer that measures the vibrations associated with heart sounds. When present in an implantable device, an accelerometer can provide for continuous monitoring of heart sounds. An implantable heart sound sensor may also be an implantable acoustic sensor or an implantable microphone; however; these are generally just other names for, or other types of, accelerometers. These devices operate by converting mechanical vibrations into an electrical signal. In some embodiments, the accelerometer is located in the can of an implantable medical device. In other embodiments, an accelerometer is located elsewhere within a patient's body and is in wireless or wired communication with an implantable medical device.

There is a correlation between blood glucose levels and cardiac activity. Not wishing to be bound by theory, it is understood that when there is a relatively greater amount of glucose in a patient's bloodstream, cellular membranes change in a manner that results in greater amounts of potassium diffusing into the cells. This in turn results in a reduction in the concentration of potassium in the bloodstream, which then affects the action potential of cardiac cells. These changes in glucose level translate into measurable changes in cardiac activity and associated electrical signals. For example, in a hyperglycemic state, it is observed that the ST-segment exhibits significant deviation relative to a baseline, and the $QT_{max}$ and $QT_{end}$ both lengthen relative to a baseline. In one embodiment, a significant deviation is generally one that is greater than or equal to about 10 percent. However, in other embodiments, the magnitude of the deviation may be different, and may be empirically determined and may be a parameter that is set according to the judgment of a physician or other trained person and the results or performance desired. Lengthening (or shortening) of $QT_{max}$ and $QT_{end}$ generally refers to any non-trivial change, such as in one embodiment a change of greater than or equal to about 1 percent. However, in other embodiments, the magnitude of the change may be different and may be determined based on empirical analysis and the exercise of judgment on the part of a physician. In a hypoglycemic state, the ST-segment exhibits significant deviation but there is little or no $QT_{max}$ and $QT_{end}$ lengthening. As a related matter, it has also been determined that during cardiac ischemia, the ST-segment exhibits significant deviation, the $QT_{max}$ shortens, and the $QT_{end}$ shows little or no change.

Furthermore, and again not wishing to be bound by theory, it is believed that the altered metabolics of a diabetic patient tend to affect the contractility and stiffness of the cardiac muscle. In particular, it is believed that changes in the blood glucose levels of a patient in turn affect the contractility and stiffness of the heart. Accordingly, by the Frank-Starling mechanism these changes in contractility and stiffness tend to affect relaxation and diastolic filling, which are two contributors to the S2 sound. Thus, it is believed that changes in patient's glucose level can change the S2 heart sound, including its intensity (the maximum amplitude of the S2 sound) and its total length.

One problem that occurs in monitoring a patient's electrocardiogram is that the T wave can be difficult to detect. More particularly, it can be difficult sometimes to differentiate between the QRS complex and the T wave in some patients and with some devices. In some cases, the QRS complex is identified by setting a voltage threshold, such that when the electrocardiogram exceeds the threshold the QRS complex is detected. However, if the voltage threshold is set too high, some QRS complexes may be missed. Likewise, if the threshold is set too low, the T wave may be detected as a QRS complex. It may not be possible to set the threshold such that these problems are reliably avoided. In some cases, the controller of an implantable CRM device is designed to filter out the T wave, but sometimes the filter is not able to accurately differentiate between the QRS complex and the T wave.

Where a patient has an implanted medical device such as an implanted cardioverter defibrillator (ICD), the device may interpret both the QRS complex and the T wave of a single heart beat as actually two separate beats, thereby measuring a heart rate that is twice what the heart rate actually is. Under these circumstances, the ICD may determine that a state of tachycardia exists and deliver a shock to the patient's cardiac tissue in an attempt to restore a normal heart beat, when in reality this is not necessary. Also, in some cases, the T wave can be affected by medications that the patient has taken, causing measurements based on a sensed T wave to be inaccurate.

Figure 2:
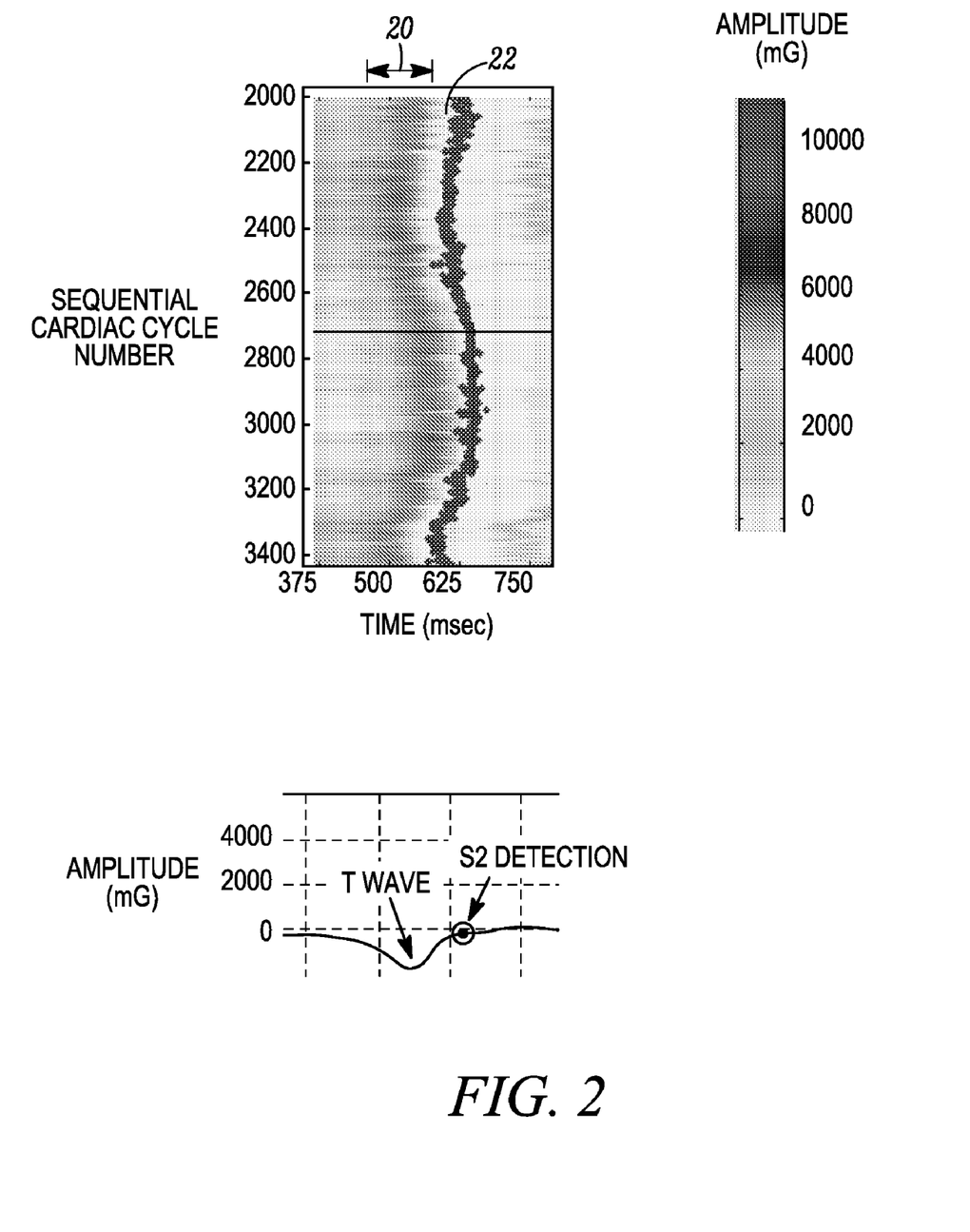
FIG. 2 is a data plot demonstrating the correlation between the T wave and the S2 heart sound.

The inventors have devised a technique that avoids these difficulties by using heart sounds instead of electrocardiogram signals to detect the state of glycemic control in a patient. The inventors have determined that the S2 heart sound closely tracks the T wave in a manner that allows S2 to serve as the basis for determining the state of glycemic control in a patient. For example, FIG. 2 depicts graphically the correlation between the T wave and S2. The top plot shows a sequence of electrocardiograms superimposed with heart sound data from an accelerometer. Each of the sequence of electrocardiograms are normalized to a beginning point and are plotted very close together. The magnitude of the electrocardiogram at any given point is represented by the shading. In this way, both axes of the plot represent time, where the X axis (horizontal) represents the time duration of any single electrocardiogram over a single heart beat, and the Y axis (vertical) represents the time duration over which all of the sequences were measured. Dark spots are used to indicate when the S2 heart sound is detected. The dark grey region labeled 20 represents the T wave portion of the electrocardiograms. The black region labeled 22 represents the detection of heart sound 22. The dark region labeled 24 represents the QRS complex. As can be seen in FIG. 2, the time between the T wave and the QRS complex varies through the range of sequences along the Y axis. However, as the position of the T wave changes, the position of the S2 heart sound tracks the position of the T wave. This data demonstrates the suitability of using S2 to determine the glycemic state of a patient, without having the difficulty or potential inaccuracy of sensing the T wave.

Figure 5:
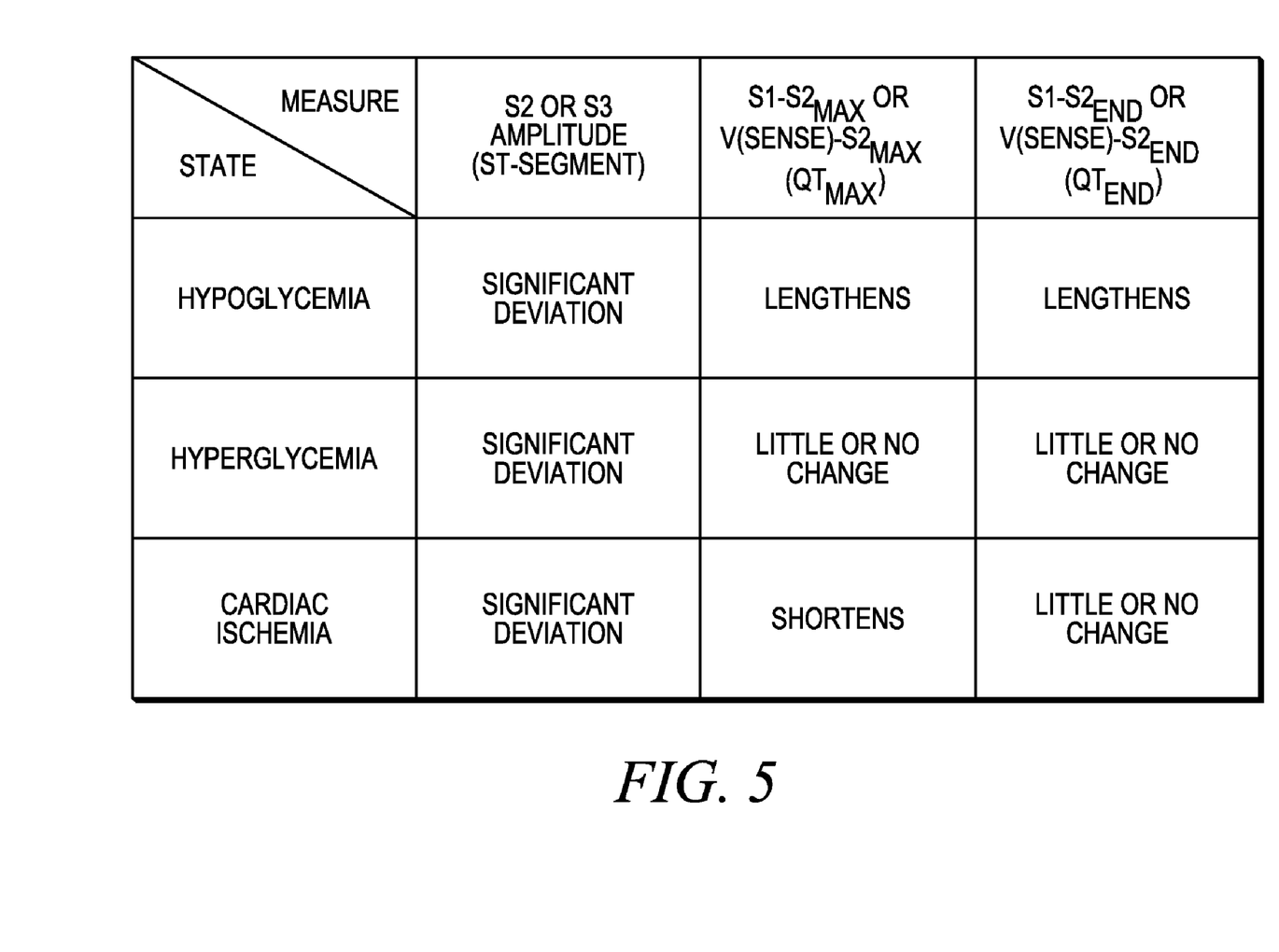
FIG. 5 is a chart depicting the relationships between heart sounds and hyperglycemia, hypoglycemia, and ischemia.

A patient in a hypoglycemic state will be expected to have significant deviation in the maximum amplitude of the S2 heart sound (or S3 heart sound) relative to a baseline. A baseline is typically a measurement that is made at a single point in time or a set of measurements over a period of time when the patient's glucose levels are relatively stable. Moreover, a patient in a hypoglycemic state will tend to exhibit lengthening in the time from S1 to $S2_{max}$, and in the time from S1 to $S2_{end}$. Furthermore, a patient in a hyperglycemic state will tend to exhibit significant deviation in the amplitude of the S2 or S3 heart sound, but little or no change in the time from S1 to $S2_{max}$ or from S1 to $S2_{end}$. As an additional piece of information, a patient having ischemia will exhibit significant deviation in the amplitude of the S2 or S3 heart sound, shortening of the S1 to $S2_{max}$ interval, and little or no change in the time from S1 to $S2_{end}$. Alternatively, each of these time measurements described herein that begin at S1 can begin instead at a sensed time corresponding to a portion of the QRS complex, such as a parameter sensed by a sense amplifier of a CRM device. In some cases, this sensed parameter can be referred to as $V_{sense}$. A chart depicting these relationships is shown in FIG. 5.

In addition, it is believed that a patient in a hypoglycemic or hyperglycemic state will exhibit an S2 heart sound having an amplitude that deviates from a baseline. This deviation in the amplitude of the S2 heart sound can therefore be used as an indicator of the state of glycemic control in the patient.

Determination of Baseline Heart Sounds Data

One way to determine whether a patient is hypoglycemic or hyperglycemic is by establishing baseline data and then comparing later measurements to that baseline data. For example, a baseline measurement can be recorded when the patient is in a known state, such as immediately after the patient's glucose level has been checked and determined to be acceptable or at a suitable mid-level value. This may include determining a baseline amplitude of the S1 and S2 heart sounds, a baseline time interval from S1 to $S2_{max}$, from S1 to $S2_{end}$, from $V_{sense}$ to $S2_{max}$ and/or from $V_{sense}$ to $S2_{end}$. Then future measurements of heart sounds can be compared against these baselines to determine whether the patient is in a hyperglycemic state or a hypoglycemic state. For example, a threshold may be established that is an increment or a percentage change from the baseline, such that a measurement that exceeds the threshold causes a determination to be made that the patient is hypoglycemic or hyperglycemic. In some embodiments, a degree of glycemic imbalance can be determined based on how far the measured values differ from the baseline values. In some cases, the trend in measured values are monitored to predict the patient's glycemic control status. Since glucose is generally consumed at a gradual pace, a trending analysis can be used to predict when a patient will reach a hypoglycemic or hyperglycemic state.

In some embodiments, the determination of whether a patient's heart sounds amplitudes and/or intervals deviate from a baseline is made over the course of a relatively small number of cardiac events, such as two or more cardiac cycles. In some other embodiments, the determination of whether a patient's heart sounds deviate from a baseline is made over the course of a greater number of cardiac events, such as the cardiac events that occur within an hour or more.

It is also possible to use the same types of analysis to determine whether ischemia is present in the patient. As described above, ischemia produces measurements that are similar to those that result from a hypoglycemic or hyperglycemic state, such as the deviation of the S1 or S2 amplitude. However, ischemia is differentiated from a hypoglycemic state or hyperglycemic state by the shortening of S1 to $S2_{max}$ accompanied by little or no change in S1 to $S2_{end}$.

Implantable Medical Device

Figure 3:
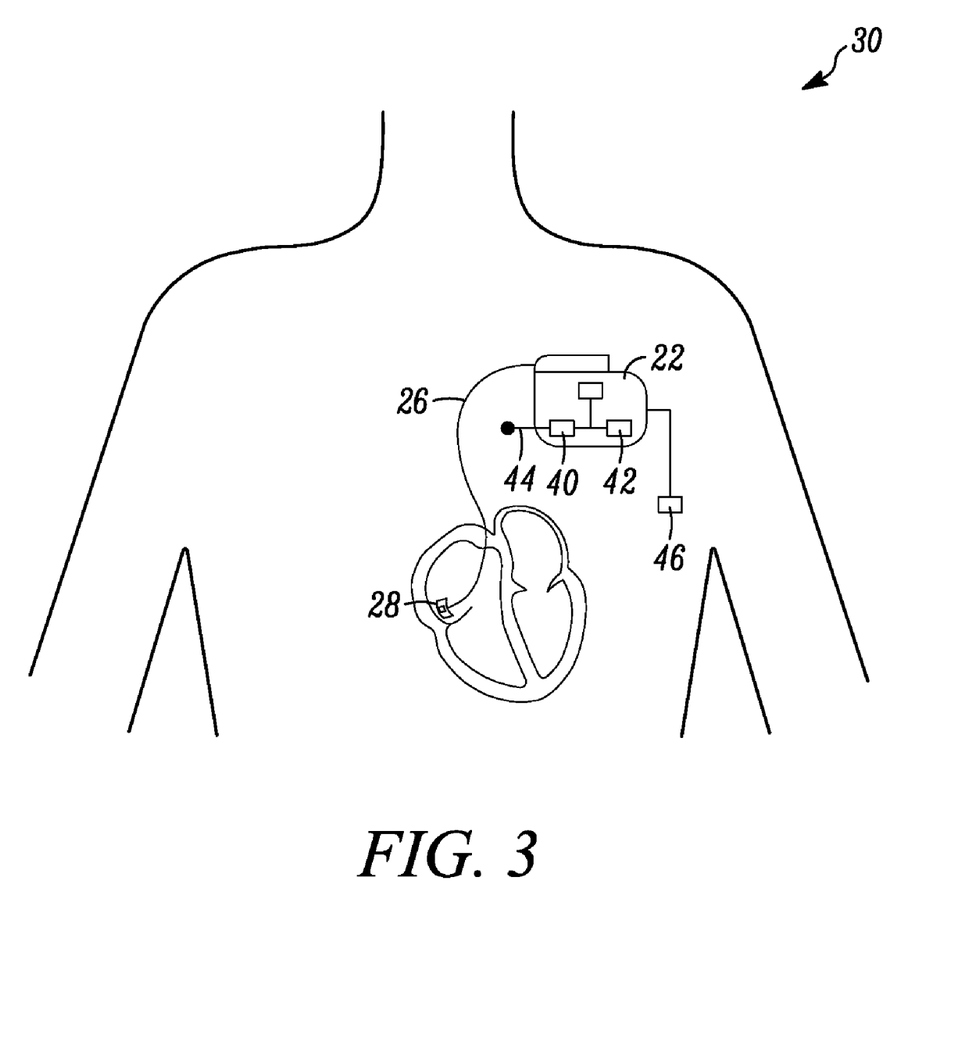
FIG. 3 is a schematic of an implantable medical device configured to monitor a patient's glycemic status.

An embodiment of an implantable medical device system constructed according to the principles of the invention is depicted in FIG. 3. The medical device system 30 includes an implantable medical device 32 such as a cardiac rhythm management (CRM) device. CRM devices may be, for example, a pacemaker, an implantable cardioverter defibrillator, or a cardiac resynchronization therapy (CRT) device. Other types of CRM devices are usable, however. CRM device 32 has at least one lead 26 that forms an electrically conductive path to an electrode 28. Electrode 28 is in contact with cardiac tissue and is capable of sensing cardiac electrical activity. A cardiac electrical signal is transmitted from cardiac tissue to electrode 28 and through lead 26 to CRM device 22, where it is received and forms the basis of an electrocardiogram that is indicative of the operation of the patient's heart. In addition, the implantable medical device 22 includes controller 40 that is capable of monitoring the cardiac electrical signals received from electrode 28 and lead 26. Controller 40 is capable of determining a heart rate from the cardiac electrical signals, as well as determining various electrocardiogram intervals, such as R-R interval and QT intervals. CRM device 22 is further configured to communicate by telemetry with appropriately configured devices outside of the patient's body. CRM device 22 further includes a heart sound sensor 42. In one embodiment, heart sound sensor 42 is an accelerometer. In another embodiment, heart sound sensor 42 is a microphone. Heart sound sensor 42 converts mechanical vibrations into an electrical signal that is provided to controller 40. Heart sound sensor 42 is generally associated with a sensitivity, such as about 1 MG/MV. Controller 40 is configured to determine the timing and the amplitude of heart sounds based on the input from heart sound sensor 42. In an embodiment, the CRM device 22 also includes an antenna 44 for communicating by way of telemetry with suitably configured devices outside of the patient's body.

Figure 4:
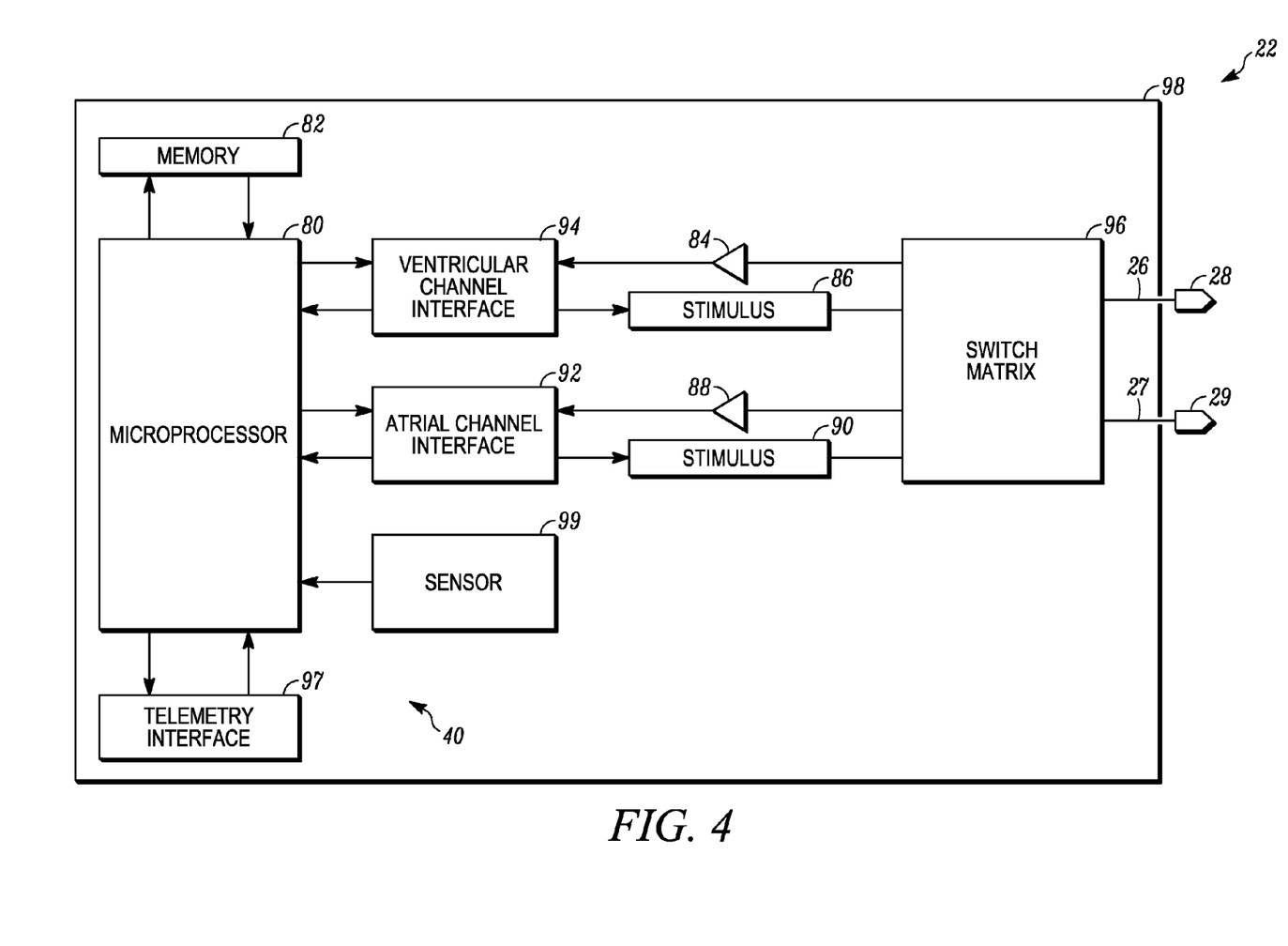
FIG. 4 is a schematic representation of functional elements of an embodiment of an implantable medical device.

FIG. 4 is a schematic depiction of the functional elements of one embodiment of a CRM device. Implantable medical device 22 is shown having lead 26 that forms an electrically conductive path to electrode 28. Electrode 28 is in contact with cardiac tissue and is capable of sensing cardiac electrical activity. A cardiac electrical signal is transmitted from electrode 28 through lead 26 to CRM device 22, where it is received and forms the basis of an electrocardiogram that is indicative of the operation of the patient's heart. Some embodiments of a CRM device have two leads and two electrodes, such as second lead 27 and second electrode 29. As shown in FIG. 4, a CRM device 22 may be further configured to communicate by telemetry with appropriately configured devices outside of the patient's body.

A controller 40 of CRM device 22 senses cardiac events through a sensing channel and outputs pacing pulses to the heart via a pacing channel in accordance with a programmed pacing mode. A microprocessor 80 serves as the controller in the embodiment of FIG. 4 and communicates with a memory 82 via a bidirectional data bus. The memory 82 typically comprises a ROM or RAM for program storage and a RAM for data storage. The implantable medical device is shown in FIG. 4 as having two leads, each having a tip electrode. Alternatively, bipolar leads are provided with ring and tip electrodes.

The implantable medical device of FIG. 4 has atrial sensing and pacing channels comprising electrode 27, lead 29, sensing amplifier 88, output circuit 90, and an atrial channel interface 92 which communicates bidirectionally with a port of microprocessor 80. In this embodiment, the device also has ventricular sensing and pacing channels comprising electrodes 28, lead 26, sensing amplifier 84, output circuit 86, and ventricular channel interface 94. For each channel, the same lead and electrode are used for both sensing and pacing. A switch matrix 96 may configure a channel for unipolar sensing or pacing by referencing an electrode of a unipolar or bipolar lead with the implantable medical device housing or can 98. The channel interfaces 92 and 94 include analog-to-digital converters for digitizing sensing signal inputs from the sensing amplifiers and registers which can be written to by the microprocessor in order to output pacing pulses, change the pacing pulse amplitude, and adjust the gain and threshold values for the sensing amplifiers. The implantable medical device can also include one or more sensors 99, such as a heart sound sensor 42. Sensors 99 may be an accelerometer, a posture sensor, an impedance sensor, a minute ventilation sensor, a pressure sensor, or the like. A telemetry interface 97 is also provided for communicating with a non-implanted device, such as through an antenna 44.

Some embodiments may include activity sensors, posture sensors, and/or time of day clocks. Determination of a patient's condition are preferably made when the patient is at rest and/or at the same time of day for consistency and accuracy of the determination. Embodiments of activity sensors include heart rate sensors, respiration rate sensors, and blood pressure sensors. If an activity sensor is included, the signal is provided to the controller 40, which then temporarily delays making a determination of a glycemic state (or ischemic condition) if the activity sensor signal indicates that the patient is physically active. In some embodiments, a threshold value is provided that the sensor signal is compared against. Embodiments of a posture sensor include an accelerometer. If a posture sensor is present, the signal is provided to controller 40, which then temporarily delays making a determination of glycemic state or ischemia if the posture sensor indicates that the patient is not in an appropriate posture. For example, the controller may be configured to only make determinations of the patient's condition when the posture sensor indicates that the patient is in a generally vertical posture, or alternatively, only when the patient is in a generally horizontal posture.

Some embodiments may include a time of day clock. In embodiments where a time of day clock is provided, the controller 40 may be configured or be configurable to make a determination of glycemic state at only certain times of day. For example, the controller may be configured to only determine the patient's glycemic state during the patient's normal sleeping hours when the patient is presumed to have not eaten for a period of time. Some embodiments include a patient control that allows the patient to initiate a determination of glycemic state on demand. For example, a patient may initiate a demand to the controller 40 to determine the patient's glycemic state at certain times, such as shortly after a meal or after the patient has not eaten for a period of time. This could allow the patient to receive information that would allow the patient to take appropriate actions to regulate his or her blood glucose level.

Determination of Glycemic State of Patient

In an embodiment, controller 40 is configured to detect whether S2 or S3 increases in amplitude relative to a baseline. If the amplitude does not increase, the controller 40 continues to monitor the S2 or S3 heart sounds until the amplitude increases a predefined amount above the baseline. When an amplitude is detected above the predefined amount, the controller 40 is configured to determine whether the time between S1 and $S2_{end}$ has increased relative to the baseline by a predefined amount, and if so, to make a determination that the patient is hypoglycemic. Similarly, when an amplitude is detected above the predefined amount, the controller 40 is configured to determine that the patient is likely in a state of hyperglycemia when the time between S1 and $S2_{max}$ lengthens. In some embodiments, if the amplitude has increased above the predefined amount and the time between S1 and $S2_{max}$ decreases, then controller 40 determines that ischemia is likely.

Figure 6:
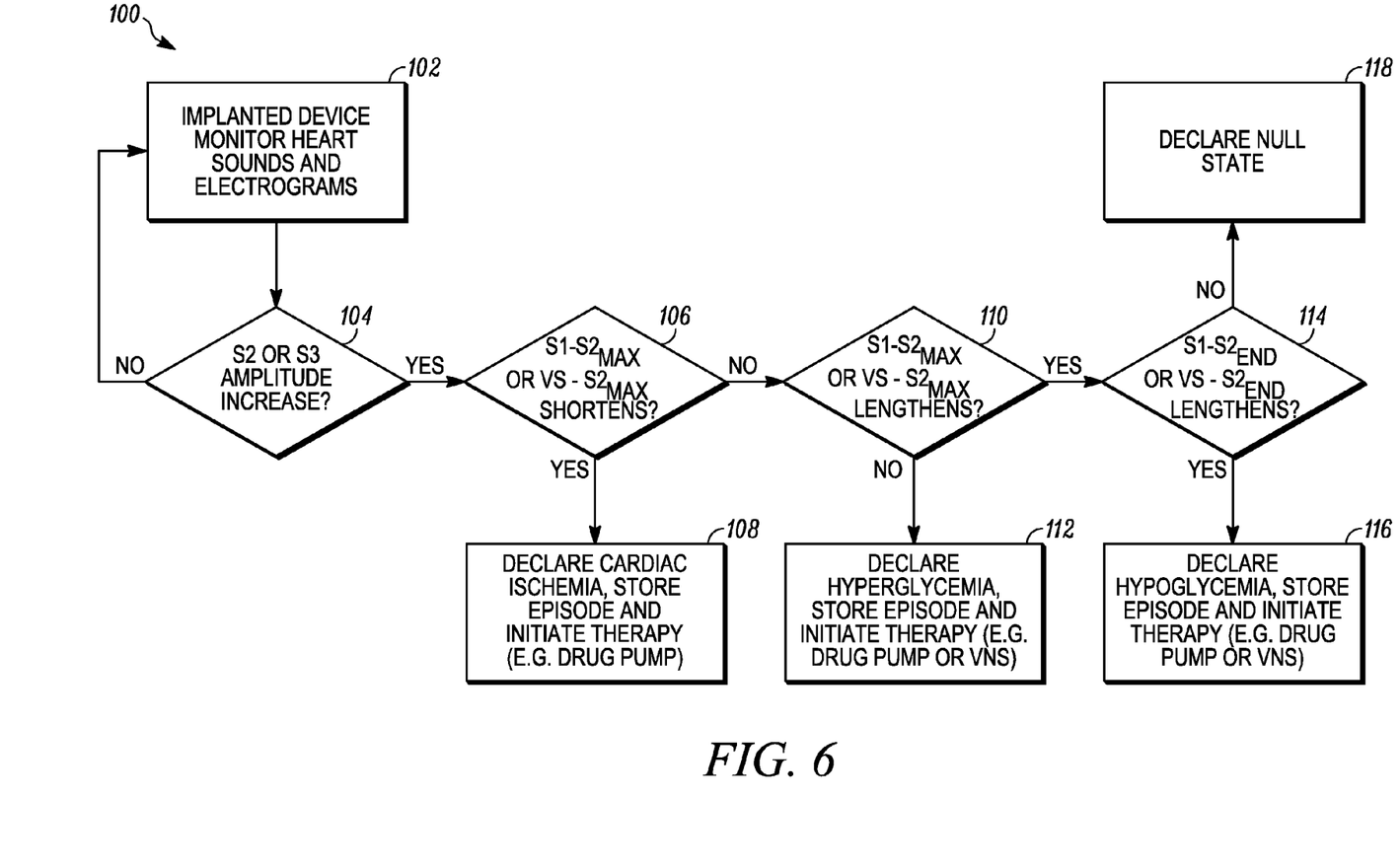
FIG. 6 is a flow chart of a method for using an implantable medical device to monitor a patient's glycemic status.

Another aspect of the invention relates to a method for detecting the glycemic control status of a patient. An embodiment of a method 100 for detecting glycemic state is depicted in FIG. 6. At step 102, an implantable medical device monitors heart sounds and electrocardiogram signals from one or more sensors. At step 104, the implantable medical device determines whether S2 or S3 heart sounds have increased in amplitude relative to a baseline or target. If not, then the device continues to monitor. If so, then at step 106, the implantable medical device determines whether the time interval from S1 to $S2_{max}$ has shortened, or alternatively, whether the time interval from $V_{sense}$ (the sensing of the QRS complex via an electrocardiogram signal) to $S2_{max}$ has shortened. If so, then the implantable device determines at step 108 that a state of cardiac ischemia exists, stores the existence of this state in memory, and initiates therapy or transmits a message. If not, then at step 110, the implantable medical device determines whether the time interval from S1 to $S2_{max}$ has lengthened, or alternatively, whether the time interval from $V_{sense}$ to $S2_{max}$ has lengthened. If so, then the implantable medical device determines at step 112, that a state of hyperglycemia exists, stores this fact in memory, and initiates a therapy or transmits a message. If not, then at step 114 the implantable medical device determines whether the interval from S1 to $S2_{end}$ has lengthened. If so, then at step 116 the implantable medical device determines that a state of hypoglycemia exists, stores this fact in memory, and initiates a therapy or transmits a message. If not, then at step 118, the controller declares a null state.

In some embodiments of method 100, step 104 is omitted. Specifically, the implantable medical device continues to step 106 regardless of whether S2 or S3 heart sounds have increased in amplitude relative to a baseline or target. In this case, the determination of the glycemic state of the patient, and/or whether the patient exhibits cardiac ischemia, is based on the time intervals determined at steps 106, 110, and 114.

Figure 7:
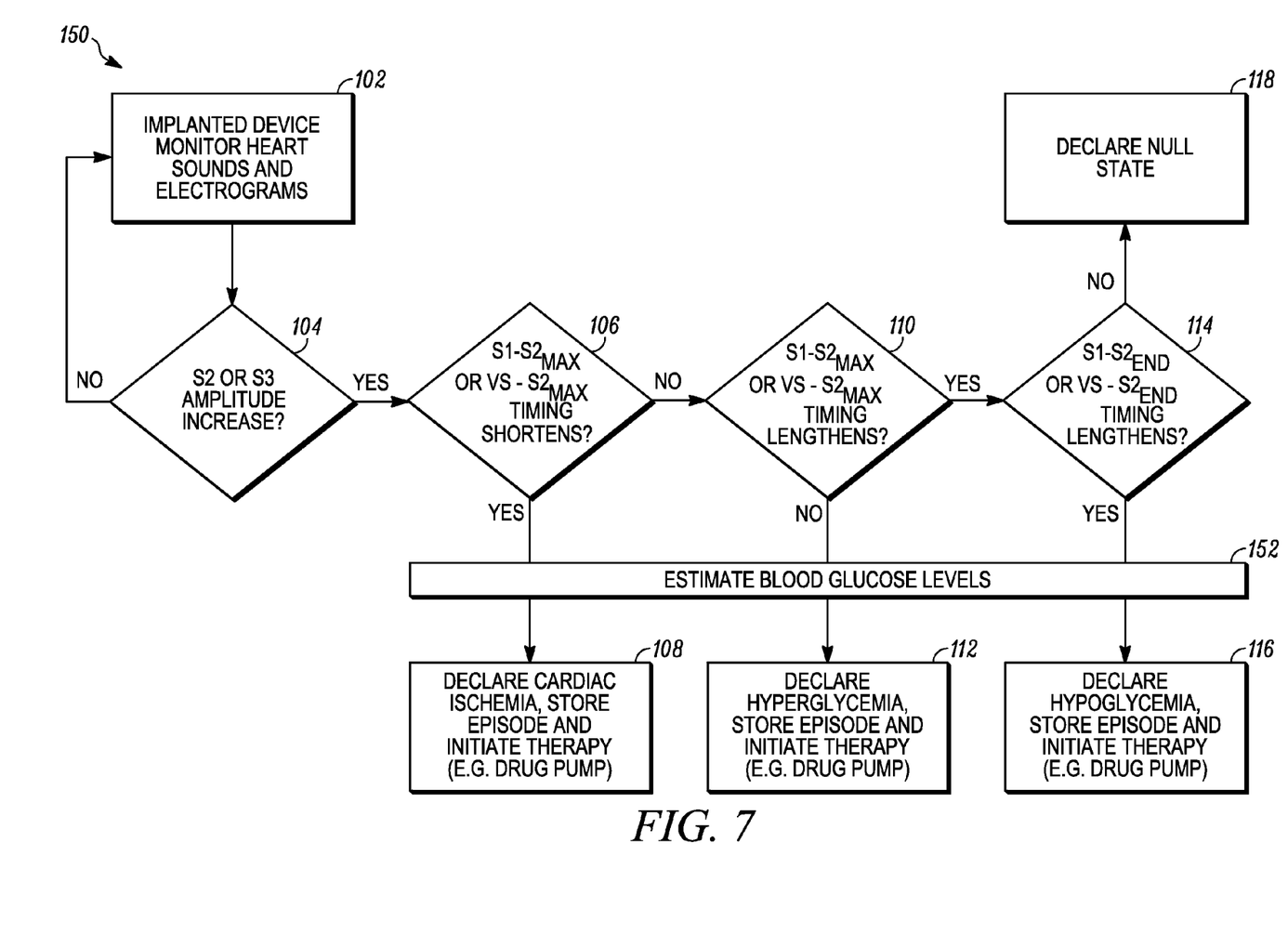
FIG. 7 is a flow chart of an alternative embodiment of the method depicted in FIG. 4.

An alternative embodiment of the method of FIG. 6 is depicted in FIG. 7. The method 150 of FIG. 7 is generally identical to method 100, except that method 150 includes a further step 152 of estimating blood glucose levels based on the sensor readings. For example, the blood glucose levels may be estimated by determining how much the various intervals or amplitudes differ from a known baseline. Generally, the greater the deviation of the S1 to $S2_{max}$ or $S2_{end}$ intervals from the baseline, the greater the glucose concentrations will be from the baseline. This relationship can be determined by developing a correlation between the various intervals and the blood glucose levels for individual patients based on monitoring of the patient.

An alternative method 160 is also useable that is a variation on methods 100 and 150. Method 160

Responses to Determination of Glycemic State

Figure 8:
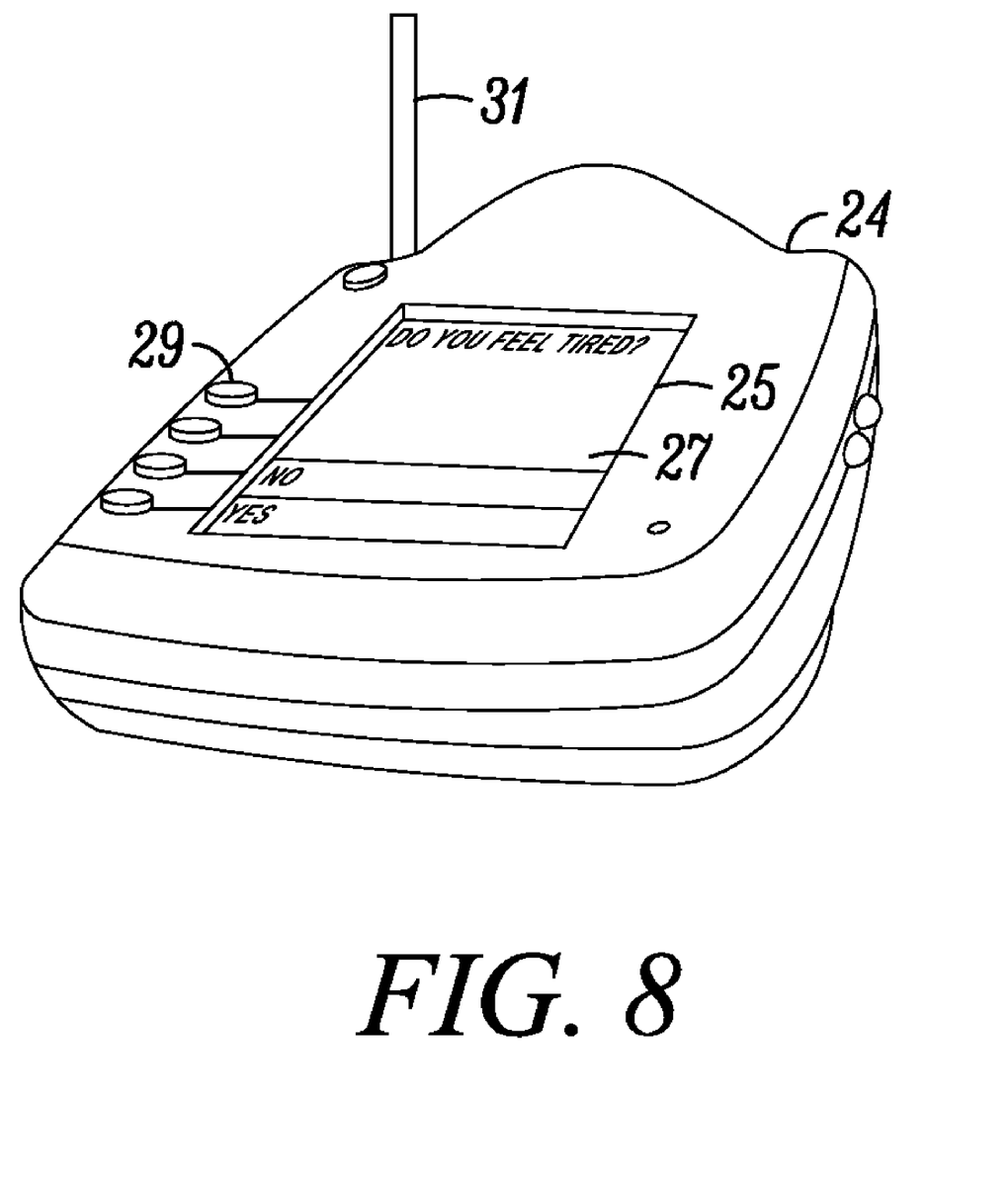
FIG. 8 is a perspective view of an embodiment of a patient interface module.

There are several potential responses to a determination of hypoglycemia, hyperglycemia, or ischemia. In one embodiment, when any one of these conditions is identified, the controller transmits a message signal, such as an audible tone that can be perceived by the patient or a telemetric signal that is transmitted from antenna 44 to an external device which can display a message that is perceptible to a person such as a patient or a doctor. An example embodiment of an external device to which a signal is transmitted is the patient interface module depicted in FIG. 8. Patient interface module 24 includes an interface 25 that is capable of displaying information and/or messages that can be perceived and understood by a patient. In the embodiment of FIG. 8, the interface 25 includes a screen 27 for displaying information. Patient interface module 24 is also capable of receiving input from a patient. In the embodiment, of FIG. 8, patient interface module 24 includes buttons 29 and screen 27 is a touch sensitive screen for receiving input. Patient interface module 24 further includes communication capabilities. Generally, patient interface module 24 is capable of communicating with an implantable medical device by telemetry. Patient interface module 24 includes antenna 31 configured for receiving and transmitting telemetric communications.

In another embodiment, the implantable medical device 32 includes communications with an implantable drug pump 46. There may be more than one drug pump 46 implanted in a patient. The drug pump may be activated by controller 40 in response to the determination of the presence of hypoglycemia, hyperglycemia, or ischemia. For example, the drug pump 46 may dispense insulin into the patient's blood stream to reduce the amount of glucose present, or may introduce drugs into the patient's blood stream to treat ischemia.

The present invention should not be considered limited to the particular examples described above, but rather should be understood to cover all aspects of the invention as fairly set out in the attached claims. Various modifications, equivalent processes, as well as numerous structures to which the present invention may be applicable will be readily apparent to those of skill in the art to which the present invention is directed upon review of the present specification. The claims are intended to cover such modifications and devices.

The above specification provides a complete description of the structure and use of the invention. Since many of the embodiments of the invention can be made without parting from the spirit and scope of the invention, the invention resides in the claims.

What is claimed is:

1. An apparatus for monitoring a patient's blood glucose level, the apparatus comprising:
   (i) an implantable medical device having a controller;
   (ii) an implantable heart sounds sensor configured to transmit signals to the controller of the implantable medical device; and
   (iii) wherein the controller is configured to determine if a patient is hypoglycemic or hyperglycemic based on the signals from the heart sounds sensor, wherein the controller is configured to detect the amplitude of an S2 heart sound from the signals from the heart sounds sensor, determine the time interval between an S1 heart sound and the time of the maximum amplitude of the S2 heart sound ($S2_{max}$), determine the time interval between the S1 heart sound and an end of the S2 heart sound ($S2_{end}$), where the controller stores baseline data derived from a signal from the heart sounds sensor and then compares signals later received from the heart sounds sensor to the baseline data to determine if a patient is hypoglycemic or hyperglycemic; and wherein the controller determines that the patient is hypoglycemic if the amplitude of the S2 heart sound deviates by a predetermined threshold from a baseline, and if both the time interval from S1 to $S2_{max}$ and from S1 to $S2_{end}$ lengthens relative to the baseline by a predetermined threshold.

2. The apparatus of claim 1, where the controller determines that the patient is hyperglycemic if the amplitude of the S2 heart sound deviates by a predetermined threshold from baseline, and if both the time interval from S1 to $S2_{max}$ and from S1 to $S2_{end}$ do not change by more than a predetermined threshold from the baseline.

3. The apparatus of claim 1, where the implantable medical device is a cardiac rhythm management (CRM) device such as an implantable pacemaker, implantable cardioverter defibrillator (ICD), or cardiac resynchronization therapy (CRT) device.

4. The apparatus of claim 1, where the implantable medical device further includes a transmitter for transmitting telemetric signals to a non-implantable device, where the implantable medical device transmits telemetric signals to the non-implantable device when the controller determines that the patient is hypoglycemic or hyperglycemic, and where the non-implantable device is configured to provide a message that is perceptible to the patient indicative of whether the patient is hypoglycemic or hyperglycemic.

5. The apparatus of claim 1, further comprising an implantable drug pump in communication with the controller, and where the implantable drug pump is configured to deliver a drug dosage to a patient in response to a determination in the controller that the patient is hypoglycemic or hyperglycemic.

6. The apparatus of claim 1, further comprising a body motion sensor configured to transmit signals to the controller, and where the controller is further configured to determine if a patient is hypoglycemic or hyperglycemic when the signal from the body motion sensor is within a predefined range.

7. The apparatus of claim 6, where the predefined range corresponds to the patient being generally sedentary.

8. The apparatus of claim 1, further comprising a body posture sensor configured to transmit signals to the controller, and where the controller is further configured to determine if a patient is hypoglycemic or hyperglycemic when the signal from the body posture sensor is within a predefined range.

9. The apparatus of claim 8, where the predefined range corresponds to a patient being in a generally horizontal posture.

10. The apparatus of claim 1, where the implantable heart sounds sensor is an accelerometer.

11. An apparatus for monitoring a patient's blood glucose level, the apparatus comprising:
   (i) an implantable medical device having a controller;
   (ii) an implantable heart sounds sensor configured to transmit signals to the controller of the implantable medical device; and
   (iii) wherein the controller is configured to determine if a patient is hypoglycemic or hyperglycemic based on the signals from the heart sounds sensor, wherein the controller is configured to detect the amplitude of an S2 heart sound from the signals from the heart sounds sensor, determine the time interval between an S1 heart sound and the time of the maximum amplitude of the S2 heart sound ($S2_{max}$), determine the time interval between the S1 heart sound and an end of the S2 heart sound ($S2_{end}$), where the controller stores baseline data derived from a signal from the heart sounds sensor and then compares signals later received from the heart sounds sensor to the baseline data to determine if a patient is hypoglycemic or hyperglycemic; and where the controller determines that the patient is hyperglycemic if the amplitude of the S2 heart sound deviates by a predetermined threshold from baseline, and if both the time interval from S1 to $S2_{max}$ and from S1 to $S2_{end}$ do not change by more than a predetermined threshold from the baseline.

12. The apparatus of claim 11, where the implantable medical device further includes a transmitter for transmitting telemetric signals to a non-implantable device, where the implantable medical device transmits telemetric signals to the non-implantable device when the controller determines that the patient is hypoglycemic or hyperglycemic, and where the non-implantable device is configured to provide a message that is perceptible to the patient indicative of whether the patient is hypoglycemic or hyperglycemic.

13. The apparatus of claim 11, where the implantable medical device is a cardiac rhythm management (CRM) device such as an implantable pacemaker, implantable cardioverter defibrillator (ICD), or cardiac resynchronization therapy (CRT) device.

14. The apparatus of claim 11, where the implantable medical device further includes a transmitter for transmitting telemetric signals to a non-implantable device.

15. The apparatus of claim 11, further comprising an implantable drug pump in communication with the controller, and where the implantable drug pump is configured to deliver a drug dosage to a patient in response to a determination in the controller that the patient is hypoglycemic or hyperglycemic.

16. The apparatus of claim 11, further comprising a body motion sensor configured to transmit signals to the controller, and where the controller is further configured to determine if a patient is hypoglycemic or hyperglycemic when the signal from the body motion sensor is within a predefined range.

17. The apparatus of claim 16, where the predefined range corresponds to the patient being generally sedentary.

18. The apparatus of claim 11, further comprising a body posture sensor configured to transmit signals to the controller, and where the controller is further configured to determine if a patient is hypoglycemic or hyperglycemic when the signal from the body posture sensor is within a predefined range.

19. The apparatus of claim 18, where the predefined range corresponds to a patient being in a generally horizontal posture.

20. The apparatus of claim 11, where the implantable heart sounds sensor is an accelerometer.

* * * * *